US006875857B2

(12) United States Patent
Simms

(10) Patent No.: US 6,875,857 B2
(45) Date of Patent: Apr. 5, 2005

(54) REAGENT FOR THE ISOLATION OF RNA

(75) Inventor: Domenica Simms, Silver Spring, MD (US)

(73) Assignee: Invitrogen Corporation, Carlsbad, CA (US)

( * ) Notice: Subject to any disclaimer, the term of this patent is extended or adjusted under 35 U.S.C. 154(b) by 15 days.

(21) Appl. No.: 10/046,667

(22) Filed: Jan. 16, 2002

(65) Prior Publication Data

US 2003/0078412 A1 Apr. 24, 2003

Related U.S. Application Data

(60) Provisional application No. 60/261,256, filed on Jan. 16, 2001.

(51) Int. Cl.[7] .............................................. C07H 21/02
(52) U.S. Cl. .................. 536/25.4; 536/22.1; 536/25.41; 536/25.42; 435/91.1
(58) Field of Search ............................. 536/25.4, 25.41, 536/25.42, 22.1; 435/91.1

(56) References Cited

U.S. PATENT DOCUMENTS

| | | | |
|---|---|---|---|
| 4,833,239 A | | 5/1989 | DeBonville et al. |
| 4,843,155 A | | 6/1989 | Chomczynski |
| 5,098,603 A | | 3/1992 | Perlman |
| 5,155,018 A | * | 10/1992 | Gillespie et al. ........... 536/23.1 |
| 5,346,994 A | | 9/1994 | Chomczynski |
| 5,585,264 A | * | 12/1996 | Babiuk et al. ............... 435/348 |
| 5,990,302 A | | 11/1999 | Kuroita et al. |

FOREIGN PATENT DOCUMENTS

| | | |
|---|---|---|
| EP | 0 727 488 A1 | 8/1996 |
| EP | 1 044 984 A2 | 10/2000 |
| JP | 61-132189 A | 6/1986 |
| WO | WO 96/34949 A1 | 11/1996 |
| WO | WO 98/45311 A1 | 10/1998 |

OTHER PUBLICATIONS

Chung et al (Molecules and Cells 6(1):108–111 (1996).*
Bahloul, M. and Burkard, G., "An improved Method for the Isolation of Total RNA from Spruce Tissues," *Plant Mol. Biol. Reporter* 11:212–215, Mary Ann Liebert, Inc. (1993).
Chang, S., et al., "A Simple and Efficient Method for Isolating RNA from Pine Trees," *Plant Mol. Biol. Reporter* 11:113–116, Mary Ann Liebert, Inc 1993.
Dong, J. G., et al., "Cloning of a cDNA encoding 1–aminocyclopropane–1–carboxylate synthase and expression of its mRNA in ripening apple fruit," Planta 185:38–45, Springer Verlag (1991).
Graham, G.C., "A Method of Extraction of Total RNA from Pinus radiata and Other Conifers," *Plant Mol. Biol. Reporter* 11:32–37, Mary Ann Liebert, Inc (1993).
Schneiderbauer, A., et al., "Isolation of Functional RNA from Plant Tissues Rich in Phenolic Compounds," Anal. Biochem. 197:91–95, Academic Press, Inc. (1991).

International Search Report for International Patent Application No. PCT/US02/01017, mailed May 29, 2002.
Pending Non–Provisional U.S. Patent Application No. 10/073,260, Simms, D., et al., filed Feb. 13, 2002.
Pending Non–Provisional U.S. Patent Application No. 09/478,456, Blakesley, R.W., filed Jan. 6, 2000.
Pending Non–Provisional U.S. Patent Application No. 09/498,897, Jesse, J., et al, filed Feb. 4, 2000.
Pending Non–Provisional U.S. Patent Application No. 09/585,580, Lin, J.–J., filed Jun. 2, 2000.
Chirgwin, J.M. et al., "Isolation of Biologically Active Ribonucleic Acid from Sources Enriched in Ribonuclease," *Biochemistry* 18:5294–5299, American Chemical Society (1979).
Supplementary European Search Report for European Patent Application No. EP 02 70 1972, 2 pages, European Patent Office, Munich, Germany, Jul. 16, 2004.
Bugos, R.C., et al., "RNA Isolation from Plant Tissues Recalcitrant to Extraction in Guanidine," *Bio Techniques* 19:734–737, Eaton Publishing Company (1995).
Dahle, C.E., and Macfarlane, D.E., "Isolation of RNA from Cells in Culture Using Catrimox–14™ Cationic Surfactant," *Bio Techniques* 15:1102–1105, Eaton Publishing Company (1993).
Hale, A.D., et al., "Comparison of four RNA extraction methods for the detection of small round structured viruses in faecal specimans," *J. Virol. Methods* 57:195–201, Elsevier Science B.V. (1996).
McIntosh, L., and Cattolico, R.A., "Preservation of Algal and Higher Plant Ribosomal RNA Integrity during Extraction and Electrophoretic Quantitation," *Anal. Biochem.* 91:600–612, Academic Press, Inc. (1978).
Nicolaides, N.C., and Stoeckert, Jr., C.J., "A Simple, Efficient Method for the Separate Isolation of RNA and DNA from the Same Cells," *Bio Techniques* 8:154 and 156, Eaton Publishing Company (1990).
Robaglia, C., et al., "Evolution and replication of tobacco ringspot virus satellite RNA mutants," *EMBO J.* 12:2969–2976. Oxford University Press (1993).

(Continued)

*Primary Examiner*—Francisco Prats
(74) *Attorney, Agent, or Firm*—Sterne, Kessler, Goldstein & Fox P.L.L.C.

(57) ABSTRACT

The present invention provides RNA extraction reagents, methods and kits that are especially useful for extracting RNA. The reagents, methods and kits of the present invention are especially useful for extracting RNA, for example, cytoplasmic RNA, from difficult materials, from plants, especially, difficult plant tissues, such as those containing phenolics, tannins, polysaccharides (such as starch) and resins. Comparative high yields are obtainable according to the present invention when compared to conventional reagents and methods. The RNA preparations obtained in accordance with the present invention are also of high quality as demonstrated by superior $A_{260/280}$ results and by gel electrophoresis.

28 Claims, 1 Drawing Sheet

OTHER PUBLICATIONS

Sambrook, J., et al., "Isolation of RNAs," in *Molecular Cloning: A Laboratory Manual*, 2nd ed., Cold Spring Harbor Laboratory, Cold Spring Harbor, NY, Sections 7:6–7.15 (1989).

Copy of co–pending U.S. Application No. 09/058,350, inventor Simms, D., filed Apr. 10, 1998.

WPI/Derwent, and PAJ/JPO English language abstracts for JP 61–132189 A.

Kunz, G.L., Office Communication for United States Patent Application No. 09/058,350, 4 pages, United States Patent and Trademark Office (mailed Mar. 3, 1999).

Esmond, R.W., Applicant's Amendments to the Claims for United States Patent Application No. 09/058,350, 5 pages, "Amendment And Reply Under 37 C.F.R. § 1.111" (filed Jun. 3, 1999).

Kunz, G.L., Office Communication for United States Patent Application No. 09/058,350, 3 pages, United States Patent and Trademark Office (mailed Aug. 16, 1999).

Vidovich, K.K., Applicant's Amendments to the Claims for United States Patent Application No. 09/058,350, 3 pages, "Amendment And Reply Under 37 C.F.R. § 1.111" (filed Feb. 16, 2000).

Owens, H., Office Communication for United States Patent Application No. 09/058,350, 6 pages, United States Patent and Trademark Office (mailed May 9, 2000).

Bugaisky, L.B., Applicant's Amendments to the Claims for United States Patent Application No. 09/058,350, 2 pages, Amendment And Reply Under 37 C.F.R. § 1.111 (filed Nov. 8, 2000).

Vidovich, K.K., Applicant's Amendments to the Claims for United States Patent Application No. 09/058,350, 3 pages, Supplemental Amendment And Reply Under 37 C.F.R. § 1.111 (filed Jan. 16, 2001).

Owens, H., Office Communication for United States Patent Application No. –9/058, 350, 6 pages, United States Patent and Trademark Office (mailed Mar. 27, 2001).

Owens, H., Office Communication for United States Patent Application No. 09058,350, 3 pages, United States Patent and Trademark Office (Jul. 28, 2001).

Owens, H., Office Communication for United States Patent Application No. 09/058,350, 3 pages, United States Patent and Trademanrk Office (mailed Oct. 31, 2001).

European Examination Report for European Application No. EP 98 91 5405.9, 3 pages, European Patent Office, The Hague, Netherlands (mailed Sep. 24, 2003).

Unverified English translation of Japanese of Publication No. JP 61–132189 A (Document AN1).

* cited by examiner a b c d e f g h a b c d e f g h a b c d e f g h a b c d e f g h

REAGENT FOR THE ISOLATION OF RNA

BACKGROUND OF THE INVENTION

1. Field of the Invention

The invention is a reagent, methods and kits for the isolation of RNA from RNA containing cells and tissues, and preferably from cells and/or tissues from plants and plant materials.

2. Related Art

Commercial reagents and kits available for the isolation of RNA do not accommodate difficult specimens, especially those specimens rich in polyphenolics (e.g., conifer needles) or starch (e.g., potato tuber or seeds). RNA yields from these reagents and kits are low, or RNA quality is poor as demonstrated by low $A_{260/280}$ ratios or gel electrophoresis.

Several methods are described in the literature for the isolation of RNA from pine needles and spruce needles that are reported to give RNA of good quality. See, e.g., Schneiderbauer, A. et al, Isolation of Functional RNA from Plants Rich in Phenolic Compounds Analytical Biochemistry 197:91–95 (1991); Graham, Glenn C., A method of extraction of total RNA from *Pinus radiata* and other conifers, *Plant Molecular Biology Reporter*, 11:32–37 (1993); Chang, Shujun, Puryear, Jeff and Cairney, John, A simple and efficient method for isolating RNA from pine trees, *Plant Molecular Biology Reporter* 11:113–116 (1993); and Bahloul, Mouna and Burkard, Gerard, An improved method for the isolation of total RNA from spruce tissues, *Plant Molecular Biology Reporter* 11:212–215 (1993).

However, all of these known methods are extremely laborious. For example, Schneiderbauer extracts pine or spruce specimen with acetone at −70° C. to remove polyphenolics. The pellet is then homogenized in the presence of 0.1% (v/v) TRITON®X-100 (octyl phenol polyethoxylate), 15 mM DTT (dithiothreitol) and phenol. The homogenization process releases RNA, DNA, and proteins. Proteins are removed by phase separation in an organic extraction phase. Then, DNA is removed by centrifugation on a cesium chloride cushion.

Another method (Graham) uses guanidinium isothiocyanate to disrupt the tissue, and RNA is then recovered by centrifugation on a cesium trifluoroacetate cushion. Other methods use cationic (Chang, et al) or anionic (Bahloul, et al) detergents to release the nucleic acids followed by either multiple alcohol precipitation or phenol extraction, and lithium chloride precipitation to remove DNA from the isolated RNA.

The reagent and methods of the present invention simplify the RNA extraction process, yielding high quality RNA from RNA containing materials, especially ordinary plant specimens and those enriched in polyphenolics and starch.

SUMMARY OF THE INVENTION

The present invention provides RNA extraction reagents, methods and kits that are especially useful for extracting RNA. The reagents, methods and kits of the present invention are especially useful for extracting RNA, for example, cytoplasmic RNA, from difficult materials, from plants, especially, difficult plant tissues, such as those containing phenolics, tannins, polysaccharides (such as starch) and resins. Comparative high yields are obtainable according to the present invention when compared to conventional reagents and methods. The RNA preparations obtained in accordance with the present invention are also of high quality as demonstrated by superior $A_{260/280}$ results and by gel electrophoresis.

BRIEF DESCRIPTION OF THE FIGURES

In FIGS. 1–4, eight assay bands are labeled a–h, wherein a–h are: (a) Blue spruce needles; (b) Scrub pine (spring shoot); (c) White pine (spring shoot); (d) Juniper; (e) Cedar; (f) Holly leaves (spring leaves); (g) Hemlock; and (h) RNA ladder.

DETAILED DESCRIPTION OF THE INVENTION

Figure 1:
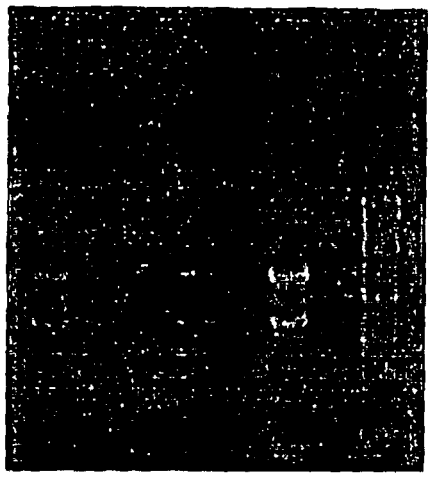
FIG. 1 shows a gel analysis of RNA isolated from Conifers and Holly using the RNeasy Format.
Figure 2:
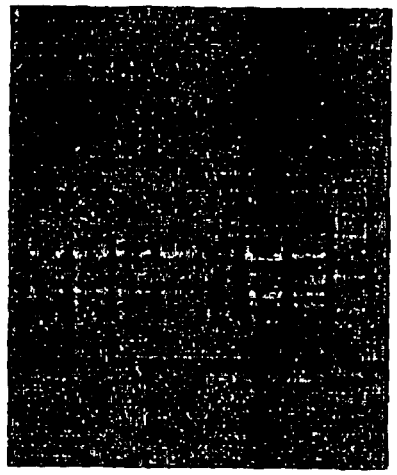
FIG. 2 shows a gel analysis of RNA isolated from Conifers and Holly using a RNA isolation reagent cartridge purification method.
Figure 3:
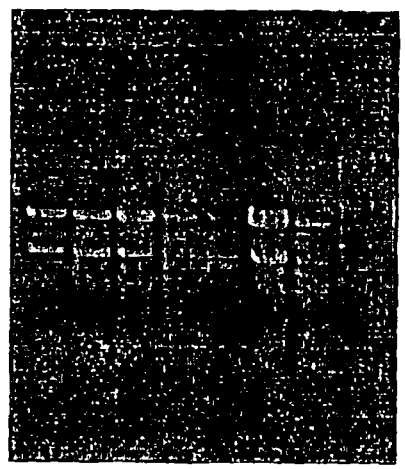
FIG. 3 shows a gel analysis of RNA isolated from Conifers and Holly using the RNA isolation reagent chloroform extraction format.
Figure 4:
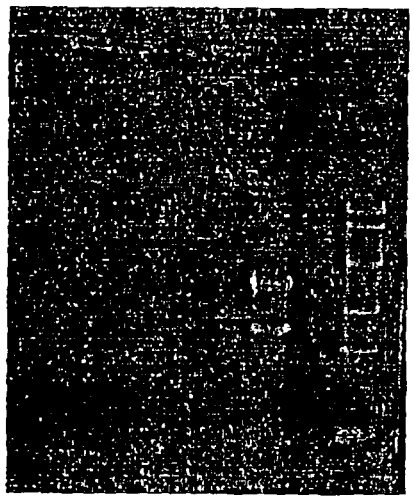
FIG. 4 shows a gel analysis of RNA isolated from Conifers and Holly using TRIzol.

The RNA Isolation Reagent of the present invention comprises, but is not limited to one or more, preferably two or more of the following components:

- one or more non-ionic detergent
- one or more ionic detergent
- one or more chelator
- one or more reducing agent
- one or more antibacterial agent (e.g., sodium azide, at about 0.5%).

The primary detergent may be any of the non-ionic detergents available, or in use: e.g., IGEPAL® (tergitol) (tert-octylphenoxy poly(oxyethylene)ethanol) (NP-40 replacement), TRITON®s, (TRITON®X-100 (octyl phenol polyethoxylate)), TWEEN®20 (polyoxyethylene sorbitan monolaurate) and like kind, etc., and is chosen for its ability to extract RNA without co-isolation of DNA. Preferably, non-ionic detergent is present at a concentration of about 0.1–4% by volume, more preferably at a concentration of about 0.5–3%, or about 1%–2%. A suitable non-ionic detergent is IGEPAL® (tergitol) (tert-octylphenoxy poly (oxyethylene) ethanol) at a concentration of 1% by volume.

The helper-detergent or secondary detergent may be any of the cationic or anionic detergents available (e.g. SDS, CTAB) and improves RNA yields especially at high reducing agent concentrations, for example, 2-mercaptoethanol concentrations of about 40%. Preferably, the concentration of ionic detergent is about 0.01%–0.5%, more preferably, at a concentration of about 0.01–0.1%. A suitable ionic detergent is SDS at a concentration of about 0.02% or up to about 0.2%, depending on the plant material and the concentrations of other components, especially the reducing agent.

The detergents are selected in an amount so as to render the cell membranes permeable so that agents can enter the cell cytoplasmic domain and RNA can exit the cell cytoplasmic domain. Preferably, the amounts of the detergents and reducing agent(s) are selected to retain degradative components within the cell so that harmful enzymes, etc., are removed with the cellular debris.

The greater the concentration of 2-mercaptoethanol or similar reducing agent in the formulation, the higher the concentration of secondary (ionic) detergent that may be included. As the 2-mercaptoethanol concentration is increased, the RNA yield decreases, but RNA is better protected, i.e., extracted of higher quality. This high quality RNA is remarkable especially for plants containing the highest levels of polyphenolics (e.g., cedar or juniper). See Tables 1–13.

The chelator may also provide the 'salt' requirement to maintain the cell membrane and/or the cell nucleus at physiological salt conditions, to avoid osmotic disruption. Chelator may be chosen from those commonly in use. For example, EDTAs, EGTAs, citrates (such as sodium citrate), citric acids, salicylic acids, salts of salicylic acids, phthalic acids, 2,4-pentanedines, histidines, histidinol dihydrochlorides, 8-hydroxyquinolines, 8-hydroxyquinoline, citrates and o-hydroxyquinones are representative of chelators known in the art. Alternatively, one component of the reagent may be used to provide the salt strength, NaCl, KCl, etc., and a different agent (e.g., betaine) may be used as the chelator.

Preferably, the chelator is present at a concentration of about 0.02–0.25 M. More preferably, the chelator is present at a concentration of about 0.05–0.2 M. A suitable chelator is EDTA at a concentration of about 0.1 M.

The reducing agent may be chosen from 2-mercaptoethanol or from any number that would replace 2-mercaptoethanol (e.g., DTT, or other mercaptans). Preferably the reducing agent is present at a concentration of about 1%–40% volume. More preferably the reducing agent is present at a concentration of about 10%–40%. 2-Mercaptoethanol at a concentration of either 20% or 40% was found to produce RNA at good yield and high quality in selected tissues. For some applications, about 4% 2-mercaptoethanol is suitable.

The antibacterial agent, e.g., sodium azide, is preferentially included to extend the shelf life of the reagent. Accordingly, an antibacterial agent is not required when freshly prepared components are combined shortly before use. Also, any antibacterial agent that extends shelf life without unduly degrading the quality of the RNA obtained is therefore suitable for use in the present invention. The amount of antibacterial agent depends on the agent and the storage conditions and should be selected so as not to interfere with the extraction process and to provide the desired shelf life.

Notably, phenol is not included in the present RNA Isolation Reagent. Phenol has been found to act as a substrate for (poly)phenolic oxidases, thereby participating in the oxidation of extracted RNA. Therefore, although components other than those listed above may be included in the Extraction Reagent of the present invention, an appreciable amount of phenol is not permitted.

All components and surfaces that might contact the sample are preferably RNase free.

A subset of the components can be prepared in advance, separately, or in combination and be combined with the remaining components at a time before use or at the time of use to obtain the working formulation.

The general protocol for isolating RNA according to the present invention is suitable for a variety of RNA containing materials, for example, plant cells or plant tissues, for example cells or tissues obtained from plant stems, leaves, roots, seeds and flowers. Plant tissue is first ground to a coarse or fine powder. When the plant material is a cell culture, the cells are mixed, e.g., by rocking, with the extraction medium for about five minutes. When the plant material is tissue material, the powder is mixed with the extraction medium for about 20 minutes. Preferably, the plant material is mixed with reagent until ground tissue is thoroughly suspended.

Finer material requires less mixing time than coarser material. Shorter mixing results in lower yields. Extended mixing provides an increased yield, but lower quality RNA. The mixing times can be adjusted depending on the plant material and the amount and quality of RNA desired.

The extract preparation is then centrifuged to remove cellular debris. A step of filtration or straining can also be used. Concentrated NaCl is then added to the preparation, for example about 0.25 parts of 5 M NaCl. An organic extraction solvent, such as $CHCl_3$ is added to the supernatant and mixed therewith. Aqueous and organic phases are separated by centrifugation. The aqueous phase is subjected to alcohol, e.g., ethanol, precipitation to obtain isolated RNA.

Two formulations were used in the examples described below as preferred formulations. Other formulations are suitable generically or for specific plant tissues. Preferred formulations are the 40% 2-Mercaptoethanol Formulation and the 20% 2-Mercaptoethanol Formulation. These preferred formulations are listed below:

| 40% 2-Mercaptoethanol Formulation | 20% 2-Mercaptoethanol Formulation |
|---|---|
| 1% IGEPAL ® (tergitol) | 1% IGEPAL ® (tergitol) |
| 100 mM EDTA | 100 mM EDTA |
| 0.2% SDS | 0.02% SDS |
| 40% 2-mercaptoethanol | 20% 2-mercaptoethanol |
| 0.5% sodium azide | 0.5% sodium azide |

The 40% 2-mercaptoethanol formulation is preferred for plants containing high levels of polyphenolics; and the 20% 2-mercaptoethanol formulation is preferred for more general applications.

The RNA extraction reagents of the present invention preferentially extract cytoplasmic RNA. The nuclear membrane is preserved retaining DNA and other nuclear components within the cell. The cell membrane is permeabilized, but maintains a degree of integrity to retain many cytoplasmic components, such as degradative enzymes, within the cell.

All patents, patent applications and publications cited herein are incorporated by reference in their entireties.

EXAMPLES

Example 1

Small Scale Protocol RNA Isolation with Chloroform Extraction

Fresh tissue, e.g., plant leaf or root, was ground to a powder in liquid nitrogen. Dried seed was ground at room temperature. All ground plant material was stored at −70° C. To 0.1 g of ground tissue was added 0.5 ml of the present RNA Isolation Reagent (e.g., 20% 2-mercaptoethanol formulation). The sample was mixed until the ground tissue was thoroughly re-suspended, and then let stand for 5 minutes at room temperature.

The sample was centrifuged for 2 minutes at 12,000×g in a microcentrifuge. The supernatant was transferred to an RNase-free tube. A 0.1 ml aliquot of 5M NaCl was added to the supernatant and the sample was mixed. An aliquot of 0.3 ml of chloroform was added and mixed. The sample was centrifuged at 4° C. for 10 minutes at 12,000×g to separate the phases. The aqueous phase was transferred to an RNase-free tube, and an equal volume of isopropyl alcohol was added. The sample was mixed and let stand at room temperature for 10 minutes. The sample was centrifuged at 4° C. for 10 minutes at 12,000×g. The supernatant was decanted, and the pellet was washed with 75% ethanol, and dissolved in water. If any cloudiness was observed, the sample was centrifuged at 12,000×g for 1 minute and the supernatant was transferred to a fresh tube.

Example 2

Small Scale Protocol With RNA Cartridge Purification

Fresh tissue, e.g., plant leaf or root, was ground to a powder in liquid nitrogen. Dried seed was ground at room temperature. All ground plant material was stored at –70° C. To 0.1 g of ground tissue was added 0.5 ml of the present RNA Isolation Reagent (e.g., 20% 2-mercaptoethanol formulation). The sample was mixed until the ground tissue was thoroughly re-suspended, and then let stand for 5 minutes at room temperature.

The sample was poured onto a Concert Homogenizer and centrifuged for 2 minutes at 12,000×g in a microcentrifuge to clarify the RNA extract. To the flowthrough was added an equal volume of guanidinium isothiocyanate and ethanol, and processed through the Concert RNA cartridge, washed, and the RNA was eluted with water, according to the protocol provided by the manufacturer.

Example 3

Large Scale Protocol for Isolating RNA from Plants

Fresh tissue was ground to a powder in liquid nitrogen. Dried seed was ground at room temperature. All ground plant material was stored at –70° C. To 1 g of ground tissue was added 5 ml of the present RNA Isolation Reagent (e.g., 20% 2-mercaptoethanol formulation), mixed until the sample was thoroughly re-suspended, and let stand for 5 minutes at room temperature. The sample was centrifuged at 4° C. for 5 minutes at 2600×g in a tabletop centrifuge. The supernatant was transferred to an RNase-free tube, passing the solution through a 100-µm nylon sieve. A 1 ml aliquot of 5M NaCl was added to the supernatant, and 3 ml of chloroform, and mixed. The sample was centrifuged at 4° C. for 30 minutes at 2600×g to separate the phases. The aqueous phase was transferred to an RNase-free tube, and an equal volume of isopropyl alcohol was added. The sample was mixed and let stand at room temperature for 10 minutes. The sample was centrifuged at 4° C. for 30 minutes at 2600×g. The supernatant was decanted, and the pellet was washed with 75% ethanol, and dissolved in water. If any cloudiness was observed, the solution was centrifuged at 12,000×g for 1 minute. The supernatant was transferred to a fresh tube and stored at –70° C.

Results

The present RNA Isolation Reagent isolates high quality RNA from a variety of RNA containing materials, especially from plant specimen including those enriched in polyphenolics and starch (see Tables 1–13 and FIG. 1). The $A_{260/280}$ ratio is low for RNA isolated using the two leading commercial RNA isolation reagents (RNeasy and TRIzol) from specimen rich in polyphenolics or starch indicating the poor quality of that RNA. Gel analysis shows that RNA isolated using the present RNA Isolation Reagent is intact whether the RNA was isolated from plants enriched in polyphenolics or not (FIG. 1).

The results shown in Tables 1–12 and FIG. 1 demonstrate that the present RNA Isolation Reagent of the present invention isolates high quality RNA from a variety of plant specimen including those enriched in polyphenolics and starch. The A260/280 ratio is comparatively low for RNA isolated using the two leading commercial RNA isolation reagents (RNeasy and TRIzol) from specimen rich in polyphenolics or starch indicating the poor quality of that RNA. Gel analysis shows that RNA isolated using the present RNA Isolation Reagent of the present invention is intact even when the RNA was isolated from plants enriched in polyphenolics (FIG. 1). RNA isolated using the present RNA Isolation Reagent has been used successfully as a template for RT-PCR and for the preparation of cDNA libraries.

Results summarized in Table 1 indicate that white pine spring shoot requires DTT, a reducing agent to obtain RNA that is sufficiently undegraded to maintain its 28S ribosomal RNA band, as determined by gel analysis. (See FIG. 1 for an example of RNA obtained in accordance with the present invention isolated by gel electrophoresis). As shown in Table 2, increasing the concentration of the reducing agent to 4% 2-mercatoethanol, the highest quality and highest RNA yield is obtained. Table 3 shows that a 4% concentration of 2-mercaptoethanol is not sufficient to maintain the integrity of RNA for more problematic conifers such as juniper and cedar which require 40% 2-mercaptoethanol. Increasing the concentration of 2-mercaptoethannol for the two pines significantly reduces RNA yields. When varying 2-mercaptoethanol concentrations were tested with tomato leaves, which are rich in polyphenolics, Table 5 shows that isolation of intact RNA was preferably accomplished with 20% to 40% concentration of the reducing agent.

Plants with normal levels of polyphenolics or starch give lower RNA yields with 40% 2-mercaptoethanol when compared with lower, e.g., 20%, amounts of 2-mercaptoethanol. Popcorn seeds yield an insignificant quantity of RNA with 40% 2-mercaptoethanol. Decreasing the 2-mercaptoethanol concentration to 20%, as well as reducing the SDS concentration to 0.02% results in a formulation useful for isolating high quality RNA from seeds (high starch content), tomato, white pine and blue spruce (high polyphenolic content) and Arabidopsis, soybean, rice, and corn that have normal levels of starch and polyphenolics.

RNA isolated using the present RNA Isolation Reagent has been used in RT-PCR and after poly(A+) selection for the preparation of cDNA libraries (data not shown).

TABLE 1

RNA Yields from 100 mg of White Pine Spring Shoot

| % IGE-PAL ® (tergitol) | 0.1 M EDTA in all assays, and Post Extraction NaCl, M Concentration | % SDS | mM DTT | RNA, µg | RNA Quality by Gel Analysis |
|---|---|---|---|---|---|
| 1 | 0 | 0 | 0 | 19.0 | Degraded |
| 2 | 0 | 0 | 0 | 17.7 | Degraded |
| 4 | 0 | 0 | 0 | 16.9 | Degraded |
| 2 | 0 | 0 | 20 | 17.9 | 28S present |
| 2 | 0 | 0.02 | 0 | 18.1 | Degraded |
| 2 | 0 | 0.02 | 20 | 22.8 | 28S present |
| 2 | 0 | 0.1 | 0 | 26.2 | Degraded |
| 2 | 0 | 0.2 | 0 | 31.3 | Degraded |
| 4 | 0 | 0 | 20 | 22.4 | 28S present |
| 4 | 0 | 0.02 | 0 | 24.8 | Degraded |
| 4 | 0 | 0.02 | 20 | 28.0 | 28S present |
| 4 | 0 | 0.1 | 0 | 19.5 | Degraded |
| 4 | 0 | 0.2 | 0 | 33.0 | Degraded |
| 1 | 0 | 0.02 | 20 | 22.6 | 28S present |

TABLE 1-continued

RNA Yields from 100 mg of White Pine Spring Shoot

| % IGE-PAL ® (tergitol) | 0.1 M EDTA in all assays, and Post Extraction NaCl, M Concentration | % SDS | mM DTT | RNA, μg | RNA Quality by Gel Analysis |
|---|---|---|---|---|---|
| 4 | .25 | 0.02 | 20 | 27.2 | 28S present |
| 4 | .5 | 0.02 | 20 | 21.4 | 28S present |
| 4 | 2.5 | 0.02 | 20 | 17.5 | 28S present |

TABLE 2

RNA Yields from 100 mg of White Pine Spring Shoot

| % IGEPAL ® (tergitol) | % SDS | mM DTT | % 2-Mercapto-ethanol | RNA, μg | RNA Quality by Gel Analysis: 28S Band Present? |
|---|---|---|---|---|---|
| 1 | 0.02 | 20 | 0 | 27.9 | Yes |
|   |      |    |   | 28.8 |     |
| 1 | 0.2 | 100 | 0 | 34.2 | Yes |
| 4 | 0.02 | 20 | 0 | 34.4 | Yes |
|   |      |    |   | 26.5 |     |
| 4 | 0.02 | 100 | 0 | 35.2 | Yes |
| 1 | 0.02 | 0 | 0.4 | 31.7 | Yes |
| 1 | 0.2 | 0 | 4.0 | 50.4 | Yes, Highest RNA Quality |
| 4 | 0.02 | 0 | 0.4 | 30.8 | Yes |
| 4 | 0.2 | 0 | 4.0 | 12.2 | yes |

TABLE 3

RNA Yields from 100 mg of Conifer Needles and Holly

| Sample | % 2-Mercapto-ethanol | RNA, μg | RNA Quality by Gel Analysis: 28S Band Present? |
|---|---|---|---|
| Blue spruce | 4 | 29.8 | Yes |
| Scrub pine | 4 | 20.0 | No |
| White pine | 4 | 42.6 | Yes |
| Juniper | 4 | 11.8 | No |
| Cedar | 4 | 18.8 | No |
| Holly | 4 | 53.2 | Yes |
| Hemlock | 4 | 33.4 | Yes |
| Blue spruce | 20 | 28.6 | Yes |
| Scrub pine | 20 | 25.2 | Yes |
| White pine | 20 | 38.0 | Yes |
| Juniper | 20 | 5.6 | No |
| Cedar | 20 | 9.9 | No |
| Holly | 20 | 80.0 | Yes |
| Hemlock | 20 | 22.0 | Yes |
| Blue spruce | 40 | 22.4 | Yes |
| Scrub pine | 40 | 15.2 | Yes |
| White pine | 40 | 8.2 | — |
| Juniper | 40 | 5.4 | Yes |
| Cedar | 40 | 9.1 | Yes |
| Holly | 40 | 56.6 | Yes |
| Hemlock | 40 | 9.5 | Yes |

TABLE 4

Comparison of RNA Yields from 100 mg of Plant Needles or Leaves Using RNA Isolation Reagent vs. Other Methods

| Sample | RNA Isolation Reagent Chloroform extraction format μg RNA ($A_{260/280}$) | RNA Isolation Reagent Cartridge Purification μg RNA ($A_{260/280}$) | TRIzol μg RNA ($A_{260/280}$) | RNeasy μg RNA ($A_{260/280}$) |
|---|---|---|---|---|
| Blue spruce | 16.0[a] (2.07) | 10.5[a] (2.08) | 0.8 (0.92) | 4.0 (1.28) |
| Scrub pine | 10.5[b] (1.92) | 17.7[b] (1.99) | 52.4 (1.07) | 2.6 (1.21) |
| White pine | 37.2[b] (2.04) | 12.8[b] (1.78) | 16.0 (1.11) | 1.6 (1.26) |
| Juniper | 18.0[a] (1.49) | 7.7[a] (1.75) | 14.4 (1.19) | 3.0 (1.33) |
| Cedar | 6.0[a] (1.52) | 8.3[a] (1.65) | 126.4 (1.23) | 3.2 (1.10) |
| Holly | 39.2[b] (1.98) | 22.6[b] (1.89) | 47.4 (2.01) | 23.6 (2.11) |
| Hemlock | 15.9[a] (1.60) | 16.5[a] (1.76) | 57.0 (1.35) | 8.6 (1.07) |

[a] 40% 2-mercaptoethanol/100 mM EDTA/1% IGEPAL ® (tergitol)/0.2% SDS
[b] 20% 2-mercaptoethanol/100 mM EDTA/1% IGEPAL ® (tergitol)/0.2% SDS

TABLE 5

RNA Yields from 1 g of Tomato Leaves

| % 2-Mercapto-ethanol | RNA, μg | RNA Quality by Gel Analysis: 28S Band Present? |
|---|---|---|
| 4 | 444 | No |
| 10 | 507 | No |
| 20 | 384 | Yes |
| 40 | 370 | Yes |

TABLE 6

RNA Yields (40% βME, 1% IGEPAL ® (tergitol), 0.2% SDS)

| Plant Tissue | RNA Isolation Reagent μg RNA ($A_{260/280}$) | RNeasy μg RNA ($A_{260/280}$) | TRIzol μg RNA ($A_{260/280}$) |
|---|---|---|---|
| Arabidopsis leaves | 37.8 (2.17) | 23.8 (2.20) | 32.8 (2.00) |
| Corn leaves | 17.7 (2.13) | 18.3 (2.16) | 32.3 (1.95) |
| Rice leaves | 7.0 (2.16) | 14.7 (2.04) | 21.5 (1.96) |
| Plum leaves | 23.0 (1.92) | 0.6 (1.28) | 12.7* (1.13) |
| Tomato leaves | 13.3 (1.99) | 1.8 (0.96) | 19.1* (1.44) |
| Tomato roots | 7.8 (2.00) | 5.3 (1.95) | 7.5 (1.73) |
| Potato tuber | 15.7 (1.98) | 2.0 (1.25) | 69.9* (1.46) |

*Represent OD's, little to no RNA present by gel analysis.

TABLE 7

RNA Yields (% DNA Contamination):

| Plant | 40% 2-ME with 1% IGEPAL ® (tergitol) 0.2% SDS 0.1% CTAB RNA, μg | 40% 2-ME with 1% IGEPAL ® (tergitol) 0.5% CTAB RNA, μg | 40% 2-ME 1% IGEPAL ® (tergitol) 0.2% SDS RNA, μg | 40% 2-ME no 1% IGEPAL ® (tergitol) 0.2% SDS RNA, μg |
|---|---|---|---|---|
| Arabidopsis leaves | 34.3 (5.5) | 44.9 (2.1) | 42.1 (2.8) | 44.7 (4.4) |
| Corn leaves | 13.3 (13.3) | 19.4 (6.7) | 17.5 (10.9) | 24.9 (16.5) |
| Rice leaves | 8.9 (14.4) | 9.0 (7.3) | 8.1 (16.3) | 11.4 (32.3) |
| White pine, spring shoot | 13.3 (1.7) | 26.6 (1.4) | 17.3 (1.4) | 14.4 (4.5) |

TABLE 8

RNA Yields (% DNA Contamination)

| Plant Leaf | 40% βME 0.2% SDS 1% IGEPAL ® (tergitol) | 20% βME 0.2% SDS 1% IGEPAL ® (tergitol) | 20% βME 1% IGEPAL ® (tergitol) | 20% βME 0.02% SDS 1% IGEPAL ® (tergitol) | 20% βME 0.5% CTAB 1% IGEPAL ® (tergitol) | 20% βME .05% CTAB 1% IGEPAL ® (tergitol) |
|---|---|---|---|---|---|---|
| Arabidopsis | 37.8 (2.8) | 52.6 (4.4) | 55.0 (5.1) | 54.0 (5.6) | 42.8 (4.7) | 53.6 (3.8) |
| Corn | 15.1 (10.9) | 24.9 (16.5) | 29.1 (9.6) | 37.8 (13.8) | 21.9 (5.7) | 30.0 (5.8) |
| Rice | 7.9 (7.6) | 19.0 (13.2) | 38.3 (18.5) | 17.0 (9.7) | 14.3 (3.5) | 33.5 (6.3) |
| Tomato | 15.8 (3.9) | 11.3 (12.0) | 12.8 (11.7) | 17.3 (13.3) | 13.7 (4.7) | 20.6 (8.5) |

TABLE 9

RNA Yields in μg from Popcorn Seeds (% DNA Contamination)

| Popcorn amount, g | 40% βME 1% IGEPAL ® (tergitol) 0.2% SDS | 20% βME 1% IGEPAL ® (tergitol) 0.02% SDS | 20% βME 1% IGEPAL ® (tergitol) 0.05% SDS |
|---|---|---|---|
| 1.0 | 1.2 (17) | 172.8 (6.6) | 199.4 (9.1) |
|  | 1.4 (71) | 178.3 (5.7) | 163.1 (10.9) |

TABLE 10

RNA Yields (% DNA Contamination): Plant Reagent* Protocol Optimization

| Tissue | Salt** | RNA Yield, μg (% DNA) |
|---|---|---|
| Sugarbeet leaf, 1 g | None | 531.3 (4.8) |
| Sugarbeet leaf, 1 g | 2.5 M Am. Acetate | 421.3 (5.6) |
| Popcorn seeds, 1 g | None | 0.0 |
| Popcorn seeds, 1 g | 2.5 M Am. Acetate | 227 (9.6) |
| Popcorn seeds, 5 g | 1 M NaCl | 1060.8 (6.4) |
|  |  | 1320.8 (5.9) |
| Potato tuber, 5 g | 1 M NaCl | 922.5 (3.7) |

*20% 2-mercaptoethanol, 1% IGEPAL ® (tergitol), 0.02% SDS, 100 mM EDTA, 0.5% sodium azide formulation
**Salt added to the clarified RNA extract before chloroform addition.

TABLE 11

RNA Yields from 100 mg of 15-Day-Old Soybean Tissues (μg)*

| Tissue | RNA Isolation Reagent | RNeasy | TRIzol |
|---|---|---|---|
| Leaves | 78.4 | 62.5 | 90.8 |
|  | 86.6 | 53.3 | 110.2 |
| Stems | 39.5 | 33.4 | 32.1 |
|  | 39.7 | 27.7 | 27.0 |
| Roots | 24.6 | 15.9 | 15.2 |
|  | 19.3 | 15.0 | 12.8 |

*20% 2-mercaptoethanol, 1% IGEPAL ® (tergitol), 0.02% SDS, 100 mM EDTA, 0.5% sodium azide formulation

TABLE 12

RNA Yields Using Plant Reagent*

| Sample | Amount, g | RNA Yield, mg |
|---|---|---|
| Arabidopsis whole plant | 20 | 9.7 |
| Tomato leaves | 10 | 5.0 |
|  |  | 3.9 |
| Rice leaves | 10 | 4.1 |
|  |  | 4.7 |
|  |  | 4.1 |
| Corn leaves | 30 | 9.5 |
| Field corn seeds | 40 | 8.0 |
| Fungal mycelia | 1 | 2.7 |

*20% 2-mercaptoethanol, 1% IGEPAL ® (tergitol), 0.02% SDS, 100 mM EDTA, 0.5% sodium azide formulation

TABLE 13

RNA Yields from 100 mg of Plant Materials (% DNA Contamination)*

| Plant Material | Conifer Reagent RNA, μg ($A_{260/280}$) | Qiagen RNeasy RNA, μg ($A_{260/280}$) | TRIzol RNA, μg ($A_{260/280}$) | Ambion/ Plant Aid RNA, μg ($A_{260/280}$) |
|---|---|---|---|---|
| Potato Tuber | 21.9 (1.6) | 1.1 (1.5) | 5.8 (1.7) | 0.0 |
|  | 31.5 (2.0) | 0.7 (1.5) | 18.4 (1.8) | 0.0 |
| Potato Leaves | 62.9 (2.0) | 46.0 (2.0) | 26.6 (1.5) | 3.0 (1.9) |
|  | 93.8 (2.0) | 38.0 (1.5) | 50.2 (1.6) | 12.0 (2.2) |
| Soybean Seeds | 27.0 (2.0) | 12.7 (2.0) | 110 (1.7) | 1.6 (1.8) |
|  | 67.4 (2.0) | 4.0 (2.2) | 112 (1.7) | 4.6 (1.2) |
| Soybean | 135.8 (2.0) | 44.1 (2.0) | 109 (1.6) | 0.8 (1.5) |

TABLE 13-continued

RNA Yields from 100 mg of Plant Materials
(% DNA Contamination)*

| Plant Material | Conifer Reagent RNA, µg ($A_{260/280}$) | Qiagen RNeasy RNA, µg ($A_{260/280}$) | TRIzol RNA, µg ($A_{260/280}$) | Ambion/ Plant Aid RNA, µg ($A_{260/280}$) |
|---|---|---|---|---|
| Leaves | 114.5 (1.7) | 43.4 (2.0) | 33.4 (1.8) | 2.5 (1.8) |
| White Pine | 21.8 (1.8) | 0.5 (1.4) | 9.3 (1.1) | 0.9 (1.4) |
| Spring Shoot | 18.3 (1.8) | 2.5 (1.5) | 10.4 (1.1) | 0.8 (1.2) |
| Blue Spruce | 13.8 (1.8) | 2.0 (1.4) | 5.1 (1.4) | 0.9 (1.2) |
| Needles | 27.4 (1.8) | 8.8 (1.0) | 2.8 (1.2) | 1.0 (1.2) |
| Tomato | 42.0 (2.0) | 10.6 (2.0) | 22.0 (1.8) | 1.9 (1.7) |
| Leaves | 179 (1.4) | 5.5 (1.9) | 25.0 (1.8) | 9.4 (1.1) |
| Arabidopsis | 148 (1.7) | 25 (1.7) | 36.0 (1.8) | 3.9 (2.0) |
| Whole Plant | 52.0 (1.9) | 30 (1.9) | 18.0 (1.7) | 3.2 (2.0) |

*20% 2-mercaptoethanol, 1% IGEPAL ® (tergitol), 0.02% SDS, 100 mM EDTA, 0.5% sodium azide formulation

What is claimed is:

1. A reagent for extraction of RNA comprising:
   about 1% IGEPAL® (tergitol);
   about 100 mM EDTA;
   about 0.2% SDS;
   about 40% 2-mercaptoethanol; and
   about 0.5% sodium azide.
2. A reagent for extraction of RNA comprising:
   about 1% IGEPAL® (tergitol);
   about 100 mM EDTA;
   about 0.02% SDS;
   about 20% 2-mercaptoethanol; and
   about 0.5% sodium azide.
3. A reagent for extraction of RNA comprising:
   about 0.5–3% IGEPAL® (tergitol);
   about 0.02–0.25 M EDTA;
   about 0.01–0.5% SDS;
   about 1–40% 2-mercaptoethanol; and
   an amount of sodium azide effective to extend the shelf life of the reagent.
4. The reagent of claim 3, comprising:
   about 1–2% IGEPAL® (tergitol).
5. The reagent of claim 3, comprising:
   about 0.01–0.1% SDS.
6. The reagent of claim 3, comprising:
   about 0.02–0.2% SDS.
7. The reagent of claim 3, comprising:
   about 0.5–0.2 M EDTA.
8. The reagent of claim 7, comprising:
   about 0.1 M EDTA.
9. The reagent of claim 3, comprising:
   about 10–40% 2-mercaptoethanol.
10. The reagent of claim 3, comprising:
    about 4–40% 2-mercaptoethanol.
11. The reagent of claim 3 free of phenol.
12. The reagent of claim 3, comprising: about 0.5% sodium azide.
13. A method for isolating RNA from plant material comprising the following:
    mixing the material with the extraction reagent according to claim 3 to form an extract.
14. The method of claim 13, further comprising the following:
    separating cellular debris from said extract to form a clarified fraction;
    organically extracting said clarified fraction to form an aqueous phase and an organic phase; and
    precipitating RNA from said aqueous phase.
15. The method according to claim 13, wherein the plant material comprises plant tissue, fungal mycelium or seed, said method further comprising pulverizing the tissue or seed to form a powder or paste.
16. The method according to claim 14, wherein the cellular debris is removed by centrifugation.
17. The method according to claim 14, wherein the organically extracting comprises chloroform extraction.
18. The method according to claim 14, wherein the precipitating comprises alcohol precipitation.
19. A method for isolating RNA from plant material comprising the following:
    mixing the material with the extraction reagent according to claim 3 to form an extract; and
    separating cellular debris from said extract to form a clarified fraction.
20. The method of claim 19, further comprising the following:
    binding said RNA to a solid matrix.
21. The method according to claim 20, wherein said binding preferentially binds mRNA.
22. The method according to claim 20, further comprising eluting said RNA from said solid matrix.
23. A method for isolating RNA from plant material comprising:
    exposing a plant material comprising a plant tissue, fungal mycelium or seed to the reagent of claim 3 to permit cytoplasmic RNA to extract from cells or cell debris of said plant material; and
    separating said cytoplasmic RNA from said cells or cellular debris.
24. The method according to claim 23, wherein the separating includes filtering or straining.
25. The method according to claim 23, wherein the separating includes precipitating RNA and collecting the precipitate.
26. A kit for extracting RNA comprising one or more of the following components:
    one or more RNA extraction reagent according to claim 3;
    one or more RNase free wash reagents;
    one or more tissue filters; and
    one or more RNase free sample holding tube.
27. The kit according to claim 26, further comprising: components for organic extraction of said RNA.
28. The kit according to claim 26, further comprising: an RNase free matrix for binding RNA.

* * * * *